(12) United States Patent
Von Der Goenna et al.

(10) Patent No.: US 7,522,270 B2
(45) Date of Patent: Apr. 21, 2009

(54) METHOD FOR DETERMINATION OF IRREVERSIBLE RADIATION DAMAGE OF OPTICAL MATERIALS

(75) Inventors: Gordon Von Der Goenna, Jena (DE); Karin Poehl, Heideland (DE); Regina Martin, Jena (DE); Lutz Parthier, Kleinmachnow (DE)

(73) Assignee: Schott AG, Mainz (DE)

( * ) Notice: Subject to any disclaimer, the term of this patent is extended or adjusted under 35 U.S.C. 154(b) by 106 days.

(21) Appl. No.: 11/440,925

(22) Filed: May 25, 2006

(65) Prior Publication Data

US 2006/0268279 A1 Nov. 30, 2006

(30) Foreign Application Priority Data

May 30, 2005 (DE) .................. 10 2005 024 678

(51) Int. Cl.
*G01N 21/00* (2006.01)
(52) U.S. Cl. ...................................... 356/72
(58) Field of Classification Search ............. 359/355; 73/865.6; 356/72
See application file for complete search history.

(56) References Cited

U.S. PATENT DOCUMENTS

| 6,061,174 | A | 5/2000 | Shiozawa et al. |
| 6,486,949 | B2 | 11/2002 | Hachdeld et al. |
| 6,587,202 | B2 * | 7/2003 | Rebhan ...................... 356/432 |
| 6,603,547 | B2 | 8/2003 | Moersen et al. |
| 6,838,681 | B2 | 1/2005 | Mayolet et al. |
| 7,170,069 | B2 * | 1/2007 | Muehlig et al. .......... 250/461.1 |
| 7,204,942 | B2 * | 4/2007 | Mayolet et al. ............ 264/1.23 |
| 7,256,887 | B2 * | 8/2007 | Muehlig et al. ............. 356/318 |
| 2005/0029470 | A1 | 2/2005 | Muehlig et al. |
| 2005/0237523 | A1 | 10/2005 | Muehlig et al. |
| 2007/0272685 | A1 * | 11/2007 | Schreiber et al. ......... 220/2.1 R |

FOREIGN PATENT DOCUMENTS

| DE | 100 50 349 | 5/2002 |
| DE | 103 35 457 | 3/2005 |
| EP | 0 875 778 | 11/1998 |
| JP | 2001 041876 | 2/2001 |
| WO | 2004/027395 | 4/2004 |

OTHER PUBLICATIONS

Alkemper, Jochen; Kandler, Jörg; Strenge, Lorenz; Mörsen, Ewald; Mühlig, Christian; Triebel, Wolfgang; Dynamic change of transmission of CaF2 single crystals by irradiating with ArF excimer laser light, 2000, Optical Microlithography XIII, Proceedings of the SPIE, vol. 4000, p. 1568-1573.*

Kohnke, G.E.; An, C.; Smith, C.M.; Holmes, P.J.; Fluence dependent transmission in a CaF2 including correlation with thermally stimulated current, 2004 Optical Microlithography XVII, Proceedings of the SPIE, vol. 5377, p. 1764-1771.*

Masafumi Mizuguchi et al: "Time-Resolved Photoluminescence for Diagnosis . . . " Optical Society of America, vol. 16, No. 7/Jul. 1999, pp. 1153-1159 (in English).

W. Tribel et al: "Evaluation of Fused Silica for DUV Laser . . . " SPIE vol. 4103, 2000, pp. 1-11 (in English).

* cited by examiner

*Primary Examiner*—Kara E Geisel
(74) *Attorney, Agent, or Firm*—Michael J. Striker

(57) ABSTRACT

The method determines the extent of irreversible radiation damage of an optical material. The method includes the following three tests to determine the extent of irreversible radiation damage: 1) the optical material is irradiated with ultraviolet radiation at a wavelength of 193 nm and the non-intrinsic fluorescence intensity at a wavelength of 740 nm is measured; 2) the optical material is irradiated with high energy laser light and a change in respective absorptions at a wavelength of 385 nm is determined before and after irradiation; and 3) the optical material is irradiated with an energetic radiation source to form all possible color centers and a difference of respective surface integrals of corresponding absorption spectra in ultraviolet spectral and/or visible spectral regions is measured before and after irradiation.

15 Claims, 3 Drawing Sheets

METHOD FOR DETERMINATION OF IRREVERSIBLE RADIATION DAMAGE OF OPTICAL MATERIALS

CROSS-REFERENCE

The invention described and claimed hereinbelow is also described in German Patent Document DE 10 2005 024 678.8, filed May 30, 2005, in Germany. The aforesaid German Patent Document provides the basis for a claim of priority of invention under 35 U.S.C. 119.

BACKGROUND OF THE INVENTION

1. The Field of the Invention

The present invention relates to a method for determining long-term stability of the transmission properties of an optical material during irradiation with higher energy densities, to a material obtained with this testing method, and to uses of the material obtained by this testing method.

2. The Related Art

Electronic computer components such as computer chips and other integrated circuits are manufactured by optical lithography. During their manufacture these circuit structures are imaged by a photomask on a support provided with a photo-lacquer, a so-called wafer, and the circuits and/or entire electronic devices including them are produced by irradiation. Since the requirements for computer performance are always increasing, increasingly smaller circuits are required. Because of that the respective circuit structures must be imaged ever more sharply, i.e. with greater resolution, which leads to the use of ever smaller wavelengths for irradiation of the photo-lacquer. However radiation with a shorter wavelength has a correspondingly higher energy.

It is also known that materials for optical elements absorb radiation passing through them so that the intensity of the radiation is generally less after passing through those materials than its initial value immediately prior to entering the materials. Moreover additional absorption and scattering effects occur at the surfaces though which the radiation passes, which similarly leads to a reduction of the transmission of the radiation. It is also known that the amount of absorption depends not only on the wavelength of the radiation, but also on the energy density or the fluence. When the path length of a light beam through the entire optical material of a lens system can be longer than a meter without more during irradiation of these smaller chip structures or circuits, absorption of the radiation passing through the lens system is a great problem. For these optical systems it is thus desired that the absorption is kept as small as possible, i.e. these systems and their elements should have a high permeability or transmission at least for the respective working wavelengths that are used in the system. It is also known that the absorption comprises material-specific (intrinsic) parts and so-called non-intrinsic parts, which result from inclusions, impurities and/or crystal defects. Intrinsic absorption is constant and depends on the nature of the material. It is independent of the quality of the material and thus does not decrease. The additional non-intrinsic absorption depends on the quality of the material, i.e. depends on the extent of the above-mentioned impurities, crystal defects, etc and thus can be avoided, at least theoretically. It leads to quality losses in the optical material and thus in the lens system.

Energy, which leads to heating of the material, is deposited in the optical material by intrinsic and non-intrinsic absorption. This sort of heating of the material has the disadvantage that optical properties, such as the index of refraction change, since the index of refraction depends not only on the wavelength of the light but also on the temperature of the optical material, which leads to changes in the imaging behavior in an optical component used for beam formation. Furthermore heating of an optical component leads to thermal expansion and thus to a change of the lens geometry. These phenomenon produce a change of the lens focal point and to some extent blur the projected image formed by a heated lens. In photolithography, as it is used for making computer chips and electronic circuits, this causes a decrease in quality and an increase in waste and thus is not desired.

Furthermore in many materials a portion of the absorbed radiation not only is converted into heat but also into fluorescence, which similarly is produced by impurities and crystal defects.

Attempts have thus already been made to determine the optical quality of these materials prior to their processing into optical elements. Thus WO 2004/027 395 describes a method for determining the properties of an optical material used for making optical elements, in which a radiation-induced absorption is measured in an optical material by irradiating it with an exciting radiation and measuring the total fluorescence comprising the intrinsic portion induced by this exciting radiation and the non-intrinsic portion. The non-intrinsic portion of the fluorescence is determined during and/or immediately after the irradiation.

In German Patent Document DE 103 35 457.3 A1 a method is described for quantitative determination of properties of the crystals used for optical elements at high energy densities, in which the radiation-dependent transmission at wavelengths in the ultraviolet (UV) is determined by radiation-induced fluorescence. In this method at least one induced fluorescence intensity maximum is determined by measuring nonlinear absorption processes at various fluences (H), determining the slope of the transmission curve from that determination, $|dT/dH|$, and the transmission from this slope. The so-called rapid damage process RDP may be established with this method.

In German Patent Document DE 100 50 349 (A1) a method for determining the radiation stability of crystals is described. In this method the change of the absorption coefficient is measured before and after irradiation. In a first measurement the absorption spectrum A of a crystal, or of a piece of the crystal split off or cleaved from it, is measured over a predetermined wavelength range from $\lambda_1$ to $\lambda_2$ by means of a spectrophotometer. Then the crystal or cleaved piece of it is irradiated with an energetic radiation source for forming all theoretically possible color centers. After the irradiation the absorption spectrum B of the crystal or cleaved piece of it is measured in a second absorption measurement over the same wavelength range from $\lambda_1$ to $\lambda_2$. Subsequently the surface integral of the difference spectrum formed from the absorption spectra A and B over the range of wavelengths from $\lambda_1$ to $\lambda_2$ is formed and divided by the thickness D of the crystal. The absorption coefficient $\Delta k$ induced by the working wavelength used in later applications is determined from this result.

European Patent Document EP 0 875 778 A1 states that the absorption of a $CaF_2$ crystal is essentially caused by sodium impurities, which are typically in a range of about 0.1 ppm, in an image focusing optical system for a UV laser. According to that the other possible impurities, such as strontium, etc, contribute to the production of non-intrinsic absorption to an essentially small extent.

In European Patent Document EP 0 875 778 A1 a material to be tested is irradiated with an energetic ArF laser with a frequency of several hundred Hz for several seconds or minutes and the absorption spectrum prior to or after irradiation is determined. The irradiated energy per pulse amounts to 1 µJ to several Joule per pulse with a pulse duration of 10 to 20 ns. It was established that the absorption produced on irradiation of quartz glass and $CaF_2$ with a laser does not correspond with that, which is measured by the weak light beam of a spectrophotometer. Thus it was found that the permeability or transmission of the material at the start of irradiation drops comparatively rapidly until after about $10^4$ pulses and after that remains constant. Moreover it was expressly established that subsequently the transmission does not change further, so that the absorption is determined after about $10^4$ to $10^5$ pulses.

However all these methods only determine short-time reversible radiation damage. This short-time reversible radiation damage is reversible by further irradiation or heat treatment, which means that the radiation damaged structures again relax. Up to now it was thought that the irreversible radiation damage that is known to occur in quartz glass, which causes a slow and irreversible increase in absorption during long-term use of this optical material over several years, did not occur in crystals. In the meantime however long-duration tests established that irreversible permanent damage also occurs in crystals after $10^8$ to $10^9$ laser pulses at energy densities of from 5 to 25 $mJ/cm^2$ over a period of several weeks.

The current procedure for determining this permanent damage comprises determining the transmission T and/or the absorption A per input energy density or fluence H for the optical material measured and from that determining the slope of this curve $|dT/dH|$ and/or $|dA/dH|$. The amount of absolute transmission or the initial absorption at an input energy density H=0 may then be ascertained from this curve by extrapolation to 0. This value normalized to the sample thickness is characterized as the initial absorption $k_0$. Subsequently the optical material is irradiated with a higher energy density of about 1 Giga pulse with 10-12 $mJ/cm^2$ and after this irradiation as described previously the initial absorption and/or absolute transmission is determined. The difference of the respective determined initial absorptions $k_0$ (or absolute transmissions) before and after irradiation is a reliable measure for the long-term stability of the optical material. Optical materials with $\Delta k_0$ values of $>4\times10^{-4}$ $cm^{-1}$ have proven to be unusable.

Since the service life of this sort of lens system in steppers often amounts to ten years and more, a statement regarding the irreversible radiation damage that would occur over time is already required and unsuitable materials must be sorted out. Thus not only considerably costs for expensive manufacture of optical lens systems, but also illumination errors are avoided, whereby the yields during chip manufacture are increased. A simple determination of these long-term stabilities, which as much as possible is performable in a few hours, has currently not been possible and currently only occurs by the above-described pulsed laser shot method that takes several weeks.

The determination of long-term absorption increase in an endurance or stability test performed in a comparative short time has not been possible for practical reasons. Up to now no possible procedure has been found, with which a statement regarding the change of optical material properties over the entire service life can be obtained from experimental results obtained over a short time interval.

SUMMARY OF THE INVENTION

It is an object of the present invention to provide a method of the above-described kind with which irreversible or permanent absorption changes of the optical material caused by radiation damage occurring during long-term usage of the material can be quickly determined in a short time interval, in order to select a suitable material in this manner.

This object and others, which will be made more apparent hereinafter, are attained in a method of determining the extent of irreversible radiation damage of an optical material, which has a small tendency to experience such permanent radiation damage and which has a constant absorption during long-term irradiation with ultraviolet radiation of a high energy density.

According to the invention three tests are performed in order to determine the radiation damage. These three tests comprise the steps of:

a) irradiating an optical material to be determined with ultraviolet radiation at a wavelength below 250 nm, preferably of 193 nm, and determining the non-intrinsic fluorescence intensity at a wavelength of 740 nm;

b) irradiating the optical material with laser light of a high energy density and measuring a change in the respective absorptions at a wavelength of 385 nm before and after irradiation; and c) irradiating the optical material with an energetic radiation source so as to form all possible color centers and measuring a difference of respective surface integrals of the corresponding absorption spectra in ultraviolet spectral regions and/or visible spectral regions before and after irradiation.

The combination of these three special test procedures, which all indicate only the short-term immediately occurring reversible radiation damage, surprisingly may also establish whether this optical material also develops irreversible radiation damage during long-term irradiation and thus whether its absorption irreversibly increases during long duration usage. This is all the more surprising since the test procedures used here only directly indicates the rapid short-term rapidly arising reversible radiation damage, the so-called rapid damage process (RDP), which is based on a completely different mechanism than that occurring in irreversible radiation damage, which occurs during long-term usage. Only when a material fulfills predetermined set standards in all three tests is it guaranteed that no great or damaging irreversible absorption changes take place during long duration exposure to energetic radiation. For the testing procedure according to the invention the order in which the three test steps are performed is not important.

In the first test the non-intrinsic fluorescence is measured already during excitation with light and/or immediately after termination of a light pulse, i.e. after the light pulse as passed through the sample.

In a preferred embodiment of the invention in addition to the non-intrinsic fluorescence the intrinsic fluorescence is measured for standardization. Since the intrinsic fluorescence is a material constant the non-intrinsic fluorescence can be standardized from the size ratio of the non-intrinsic to intrinsic fluorescence and thus it can be rapidly determined whether the tested optical material is suitable for further processing to an optical element, such as a lens, prism, etc. Furthermore the amount of the respective impurities can be determined from this ratio with the aid of a simple calibration curve. Otherwise an expensive calibration, e.g. dimension determination, etc are required in the sample to be tested.

The procedure for performance of the method according to the invention includes determination of the fluorescence at a wavelength of 740 nm. This fluorescence band has proven to be especially sensitive in the method according to the invention. Preferably an intrinsic fluorescence band is used to normalize the non-intrinsic fluorescence. The intrinsic fluorescence band at 278 nm is especially suitable for standardization or normalization. The normalization of the height of the measured non-intrinsic fluorescence band or bands occurs by formation of the ratio of the non-intrinsic to intrinsic fluorescence (intensity). The non-intrinsic fluorescence is measured synchronized to the input laser pulses in an entirely preferred embodiment of the method according to the invention. A ratio of less than 1:100, preferably 1:200, and most preferably 1:500, shows that this optical material has passed the first test.

It has proven to be especially suitable to treat the material to be tested by means of a pre-irradiation prior to performing the method according to the invention. The absorption state of the material regarding the so-called rapid damage and/or rapid annealing is saturated with a predetermined number of laser pulses, so that the measurements following that occur from a constant base line. A typical number of laser pulses during pre-irradiation is at least 3000, preferably at least 6000 and 30,000, preferably 70,000 to 200,000. Principally it is required for performing the method according to the invention that the material is irradiated with as comparable as possible energy densities in the material to be tested. Preferably the method is performed not only with the same or comparative energy densities, but preferably with equal excitation and fluorescence wavelengths in order to obtain comparative values, especially spectra.

Finally the sort of impurities even in amounts in the ppb range can be determined without difficulties from the fluorescence spectra. The amount of the impurities producing the fluorescence spectra is determinable from the ratio of the intrinsic to non-intrinsic fluorescence. The impurity materials are usually rare earths and especially cerium, europium, terbium, sodium and oxygen from oxides.

According to the invention it is preferred to perform the irradiation in the first test step with UV light and especially far UV light. UV light with wavelengths below 250 nm, especially below 200 nm has proven to be suitable. However UV light with wavelengths between 100 or 150 nm and 200 nm is especially preferred. Appropriately the method is performed with those excitation wavelengths, with which the optical material should be irradiated during later applications. A preferred radiation source for the energetic light is a laser that produces laser pulses, preferably with working wavelengths of 193 nm.

In the method according to the invention the non-intrinsic fluorescence is preferably measured by means of a grating spectrograph and an I-CCD camera with adjustable illumination intervals (intensified charge coupled device). Preferably the obtained spectrum is processed under computer control. This type of measurement and apparatus are well known to those skilled in the art and are described, for example, by W. Triebel, et al, in Proceedings SPIE, Vol. 4103, pp. 1 to 11, (2000), "Evaluation of Fused Silica for DUV Laser Applications by Short Time Diagnostics", or also by Mizuguchi, et al, in J. Opt. Soc. Am. B, Vol. 16, 1153 and following (July 1999).

According to the invention a blocking device, which prevents the passage of the excitation radiation, is preferably arranged between the fluorescing sample to be tested and the fluorescence measuring device. This sort of blocking device, which can mask arbitrary excitation wavelengths, is known to those skilled in the art. The blocking can occur in many different ways. On possibility is to block radiation at these wavelengths by means of a grating spectrograph arranged in front of a CCD camera, which divides the received light into its different wavelengths. It is possible to block out or deflect the excitation radiation from an energetic radiation source by suitable arrangement or rotation of the spectrograph. Principally it is also possible to rotate the grating spectrograph of the CCD camera.

An additional possibility consists of the use of wavelength specific filters, such as dielectric thin film filters, which are currently selectively made for wavelengths of choice. This sort of filter is usually made by applying multiple reflecting layers on a support material, which prevents the passage of the undesired wavelengths.

Such layer filters are preferred in the method according to the invention. However it is necessary that the filter used have no self-fluorescence produced by the incident light, so that false measurement results are not produced.

The determination of the fluorescence according to the invention occurs especially within or immediately after an illumination time interval for the material. It preferably occurs within a time interval at the end of the illumination of the material, which corresponds to the respective characteristic decay curves or lifetimes of the various non-intrinsic fluorescence emissions, or is adjusted to them. In a plurality of cases 90%, especially 80%, often also 70% of the decay time has proven suitable for the measurement. In a few preferred optical materials the method according to the invention and the determination is performed within a time interval of less than 50 nsec after the end of the irradiation or the irradiation pulses in the material. However it is preferred to perform the determination within a time interval of at most 40 nsec after the end of the irradiation, but at most 30 nsec is especially preferred. In a few cases it has proven to be appropriate to complete the measurement within a time interval of less than 15 nsec, after the irradiation of the material has been performed.

The CCD cameras preferred for use in the method according to the invention are the so-called OMAs (Optical Multichannel Analyzer or intensive Optical Multichannel Analyzer), especially with adjustable illumination or measurement intervals. One such camera has a detection limit of less than 10 photons and permits a small illumination time for example 10 nsec or even down to 150 psec. This sort of camera is commercially obtainable, for example, from Roper Scientific, USA, among other sources.

The second test is performed so that the material to be tested is irradiated with high energy densities of at least 1 mJ/cm$^2$, especially at least 5 mJ/cm$^2$. Preferably the minimum energy density amounts to 25 mJ/cm$^2$, especially 50 mJ/cm$^2$. In principle, the energy density does not have an upper limit. However a maximum energy density of 200 mJ/cm$^2$, particularly of 150 mJ/cm$^2$, is suitable. However a maximum energy density of 120 mJ/cm$^2$, especially of 100 mJ/cm$^2$, is preferred. The radiation is preferably performed with a laser. An appropriate laser is a laser with a wavelength of 193 nm, e.g. an ArF laser. The energetic irradiation is suitably performed by irradiation with at least $10^4$, preferably at least $2 \times 10^4$ and especially preferably at least $3 \times 10^4$ pulses. A minimum number of $4 \times 10^4$ or $5 \times 10^4$ is especially preferred. Also an upper limit according to the invention is not relevant in the case of the number of pulses. However for practical reasons an upper limit of $20 \times 10^4$, especially $15 \times 10^4$ or $10 \times 10^4$ has proven to be suitable. Subsequently the absorption spectrum is taken in the irradiated spot and the difference in the absorption spectra before and after irradiation is determined. For this purpose the absorption spectra must be taken with radiation having as little incident energy as possible, so that the rapid radiation damage produce, i.e. the rapid damage process, does not relax again. If the differences between both of these absorption spectra exceed certain predetermined set values, then the tested material does not have the required long-term stability.

The absorption spectra are preferably taken in the ultraviolet and visible region, which means in a range between 190 nm and 800 nm. Understandably only one or a few intervals in this range are tested according to the invention, or even only one band is tested. The absorption band at 380 nm is especially preferred for quality control according to the invention. To achieve the required long-term stability for the absorption behavior the change of the absorption in this band should amount to less than 2.5 or $2\times10^{-3}$ cm$^{-1}$, preferably less than $1\times10^{-3}$ cm$^{-1}$ and especially preferably less than $0.5\times10^{-3}$ cm$^{-1}$.

In the third test for determining according to the invention whether a material to be tested has the required long-term transmission stability for use in photolithography the absorption at a peak in the spectra at a wavelength of 265 nm is measured. Then the optical material is excited, preferably with a short wavelength radiation and of course preferably as long as all or nearly all theoretically possible color centers have been formed and after that the absorption is measured again at the same wavelength as before the irradiation. It has been shown that long-term stability is then obtained when the difference of the absorption is less than $50\times10^{-3}$ cm$^{-1}$, but a difference of less than $30\times10^{-3}$, especially $20\times10^{-3}$, is preferred. However differences less than $10\times10^{-3}$ and especially less than 5 or $3\times10^{-3}$ are most preferred.

The radiation damage in conventional methods is preferably produced with those wavelengths, which would be used in the later optical elements. X-ray sources and other energetic sources are suitable radiation sources for performing the induced absorption according to the present invention. For example, radioactive Co$^{60}$ is preferred as a source of radiation because it is economical and easy to handle and readily available, but the X-ray sources are especially preferred.

The energy density required for performing the method of the invention is widely variable and depends only on the time interval in which saturation should be achieved. However usually energy densities of $10^3$-$10^5$ Gy, preferably $5\times10^3$-$5\times10^4$ Gy (1 Gy=1 J/kg), are employed. This corresponds to doses of a few 10s of J/cm$^2$, at the conditions described hereinbelow. In comparison to test 2 that over 90% of the energy is not absorbed during irradiation with a 193 nm laser beam, while a much greater percentage of the energetic radiation is absorbed in the case of X-rays must be considered. The irradiation time until saturation occurs typically amounts to 10 to 360 minutes, preferably 30 to 180 minutes. To control the saturation according to the invention a second irradiation of the sample can be performed and the intensities of the respective absorption bands or absorption spectra can be compared with each other. If no change is observed in the intensities of the absorptions, the desired saturation was reached with the radiation.

In order to guarantee that all color centers are actually excited in the optical material, the thickness of the irradiated sample or piece should not be too large, because with greater sample thickness according to the resistance of the sample to radiation uniform permeation or penetration of the entire sample with the radiation cannot be guaranteed. Also it is not possible to guarantee that the largest portion of the incident radiation is already absorbed where possible in the first part of the irradiated thickness. This would lead to different formation of color centers with distance from the sample surface, through which the incident radiation passes into the sample.

Radiation conditions should be selected at which all color centers are excited or formed. If the spectrum after irradiation is now compared with the spectrum prior to irradiation, their difference gives directly the saturation condition and shows the absorption with maximum intensity in the selected wavelength range, which can be produced with the later used working wavelength during irradiation with at that wavelength.

A great advantage of this test is that the sample or cleaved piece of crystal neither needs to be polished nor does its thickness need to be precisely adjusted. Thus any cleaved piece of the crystal can be used as the sample. Since crystals usually cleave along their crystal axes, parallel surfaces are always present, which are available for measurement of the absorption spectra with a spectrophotometer. The spacing of the surfaces from each other, i.e. the thickness of the crystal or the path length of the light in the crystal can be conventionally determined by means of a sliding caliper or micrometer screw. The light beam of the spectrophotometer preferably penetrates the crystal perpendicular to the crystal surface in order to determine the absorption or the radiation damage.

A difference spectrum, with which the resistance of the crystal to radiation is determined, is produced by measuring the amount of absorption before and after irradiation. The maximum absorption coefficient $\Delta k$[1/cm] can be calculated according to the Lambert-Beer law without more using the known distance that the radiation passes through the cleaved piece of crystal or sample. Preferred working wavelengths are those of lasers, especially excimer lasers, such as the ArF excimer laser, also 193 nm.

Preferred obtained materials include quartz and/or crystal materials. Alkali or alkaline earth halides, especially the fluorides, are preferred crystal materials. $CaF_2$, $BaF_2$, $MgF_2$, $SrF_2$, LiF, KF, and NaF are most preferred. Mixed crystals of the form $KMgF_3$ are also especially preferred. However principally other known mixed crystals, which are produced by doping a base crystal with suitable doping materials, are also suitable. Likewise cubic perovskite, cubic garnet, cubic spinel, and cubic M(II) and M(IV) oxides are suitable. Examples of the cubic garnet are of the following formulae: $Y_3Al_5O_{12}$, $Lu_3Al_5O_{12}$, $Ca_3Al_2Si_3O_{12}$, $K_2NaAlF_6$, $K_2NaScF_6$, $K_2LiAlF_6$, and $Na_3Al_2Li_3F_{12}$. $MgAl_2O_4$, $(Mg,Zn)Al_2O_4$, $CaAl_2O_4$, $CaB_2O_4$ and $LiAl_5O_8$ are examples of cubic spinel. $BaZrO_3$ and $CaCeO_3$ are examples of cubic perovskite. MgO and (Mg,Zn)O are examples of cubic II/IV-oxides.

The invention also includes the optical materials obtained using the method according to the invention and their usage in optical imaging systems. It also includes steppers, lasers especially excimer lasers, computer chips, as well as integrated circuits and electronic devices, which contain these circuits and chips, which contain optical materials that are selected or obtained using the testing method according to the invention.

BRIEF DESCRIPTION OF THE DRAWING

The objects, features and advantages of the invention will now be illustrated in more detail with the aid of the following examples, with reference to the accompanying figures in which.

EXAMPLES

Example 1

Test 1—Irradiation with a Laser Beam at 193 nm and Measurement of Fluorescence at 740 nm The changes of the initial absorption at 0 energy $\Delta k_0$ at 193 nm were measured in six crystal samples that were grown differently and that had a length of 10 mm. The respective transmission values for each sample were measured at different energy densities and the absorptions at an energy density 0 mJ/cm² were obtained by extrapolation of these measured transmission values. Subsequently they were irradiated with an ArF laser with a working wavelength of 193 nm with about 1 Giga-pulse and an energy density of 10 to 12 mJ/cm². The initial absorption was determined once again for each crystal sample after irradiation by the same method. The change is given as $\Delta k_0$.

Figure 1A:
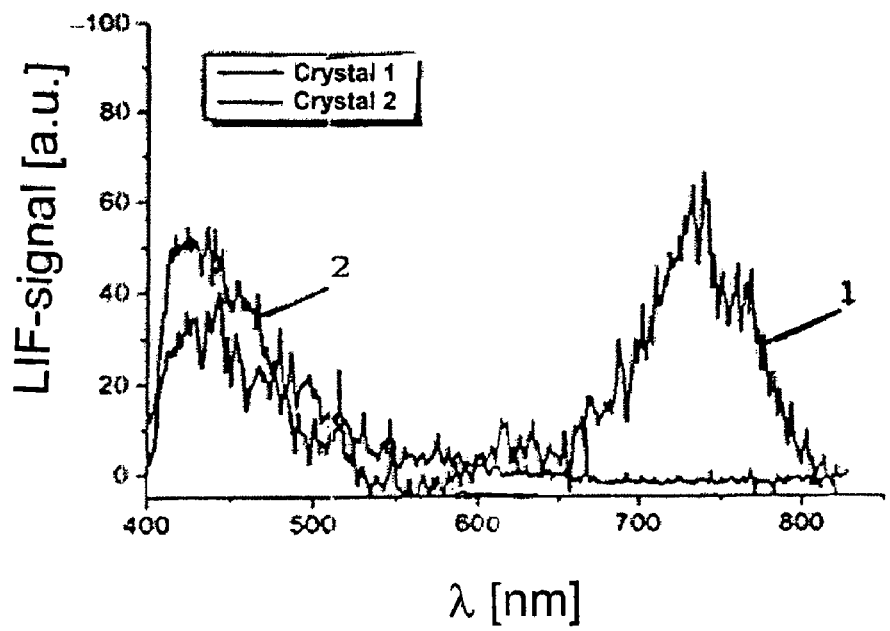
FIG. 1A shows two fluorescence spectra for crystal samples 1 and 2 taken in the first testing step of the method according to the present invention.
Figure 1B:
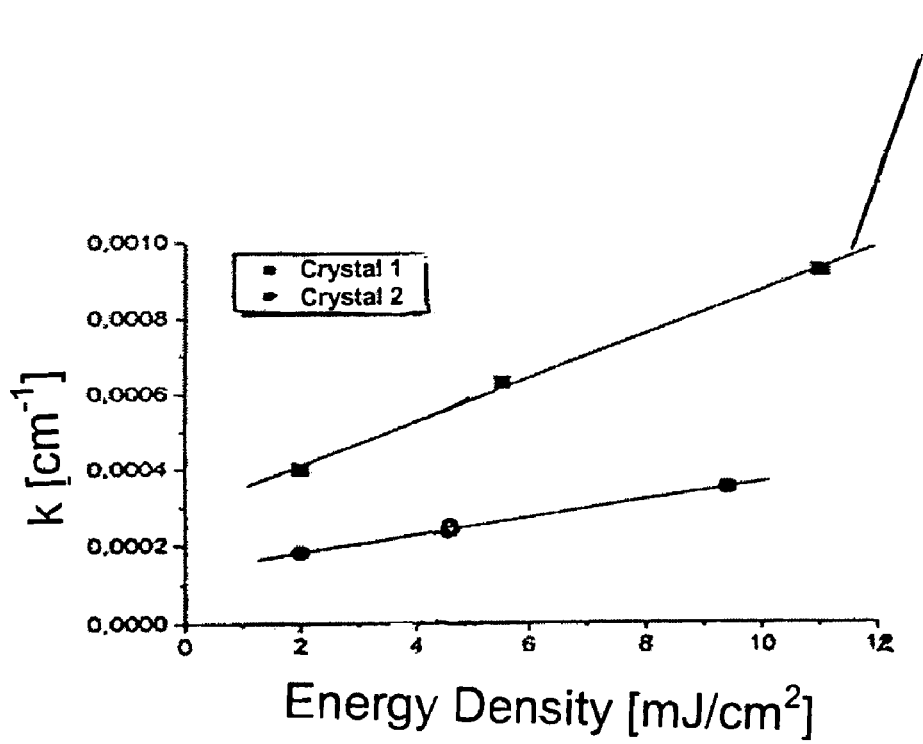
FIG. 1B is a graphical illustration showing the respective behaviors of absorbance at 193 nm versus fluence for the two crystal samples 1 and 2.

Prior to irradiation the non-intrinsic fluorescence at 740 nm was determined in crystals 1 and 2 according to the test analogous to that described in WO 2004/027395. The results are given in the added Table I. In this table it is shown that the crystal 1 is characterized by a comparatively intense fluorescence band at 740 nm, while hardly any fluorescence occurs at this location in crystal 2. The results are shown in FIGS. 1A and 1B.

TABLE I

| | $k_0$, ABSORPTION AT 0 ENERGY DENSITY &$\Delta k_0$ DUE TO IRRADIATION (Test 1) | |
|---|---|---|
| | Prior to Irradiation $k_0$ [$10^{-4}$ cm$^{-1}$] | Change due to Irradiation $\Delta k_0$ [$10^{-4}$ cm$^{-1}$] |
| Crystal 1 | 2.5 | 4.5 |
| Crystal 2 | 1.2 | 0.6 |

From this it is apparent that both crystals have a comparable initial absorption prior to irradiation. However crystal 1 has a comparative intense fluorescence band at 740 nm and then crystal 1 is not satisfy the minimum requirements for this sort of optical material according to test 1. After irradiation crystal 1 is characterized by a change of the initial absorption of $4.5 \times 10^{-4}$ cm$^{-1}$, while the change of the absorption of the crystal 2, which has hardly any fluorescence band, only amounts to $0.6 \times 10^{-4}$. This means that a material obtained from crystal 1 for lithographic applications is unusable, since it is not only characterized by a comparatively intense fluorescence band for short duration uses, but also by a strong increase in long-term damage for long-term usage and an increase in absorption associated with that increase.

Example 2

Figure 2A:
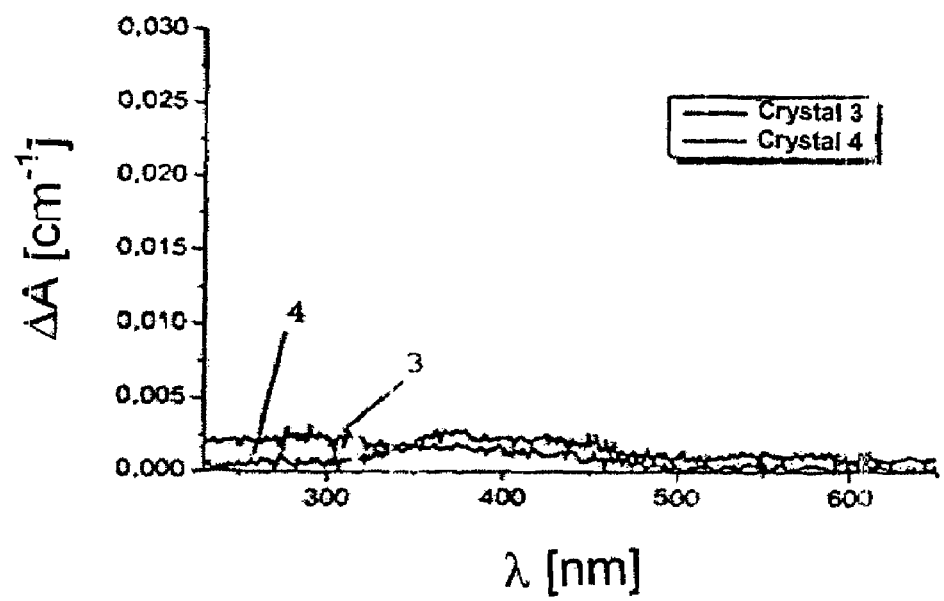
FIG. 2A is a graphical illustration showing two difference spectra for crystals 3 and 4 measured in the second testing step of the method according to the present invention.
Figure 2B:
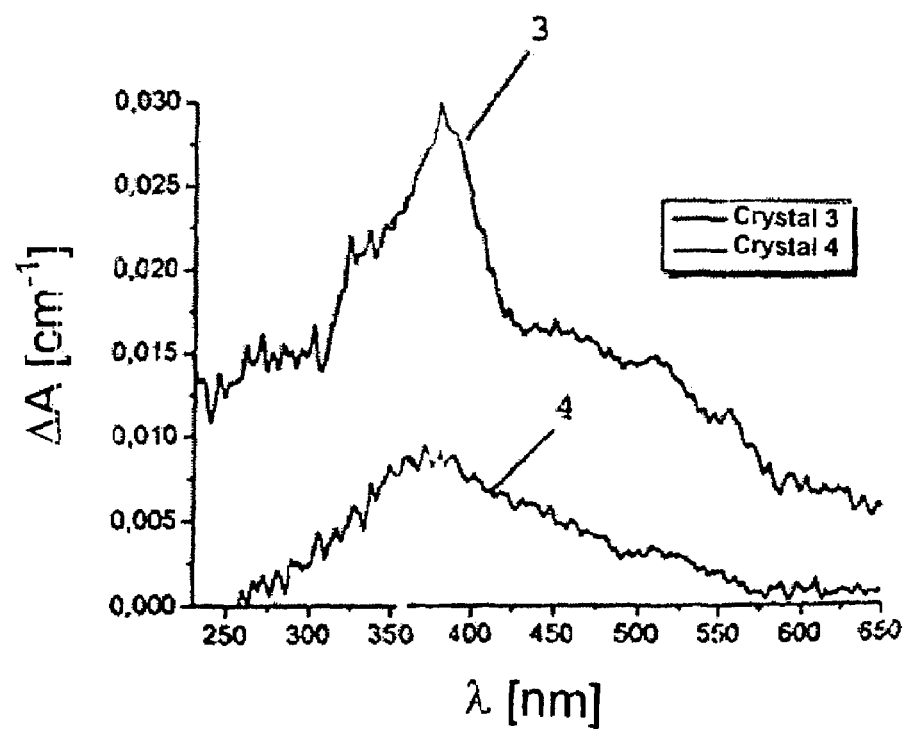
FIG. 2B is a graphical illustration showing two difference spectra for crystals 3 and 4 measured in the third testing step of the method according to the present invention.

Measurement and Change of the Spectral Properties Due to High Energy Irradiation (Test 2) and After Irradiating with X-Rays (XRD)(Test 3)

a) The procedure described here is used for crystals, which were determined to be suitable in the LIF Evaluation (Test 1). In other words the crystals tested in tests 2 and 3 are those which had hardly any or no emission bands at 740 nm as measured in test 1. The crystals 3 and 4 were tested prior to irradiation for determination of $\Delta k_0$ both with the test procedure 2 and also with test procedure 3. The results are graphically illustrated in FIGS. 2A and 2B. As shown in FIG. 2A, both crystals 3 and 4 appear to be comparable in the procedure according to test 2, however are clearly different as seen from the difference spectra as shown in FIG. 2B, which were obtained according to the test procedure 3.

After that the initial absorption prior to and after irradiation according to the invention was determined for both crystals. The results are tabulated in Table 2. The initial absorption and the absorption change were standardized or normalized after a long duration irradiation by $10^9$ laser pulses with 10 mJ/cm².

TABLE II

Figure 3A:
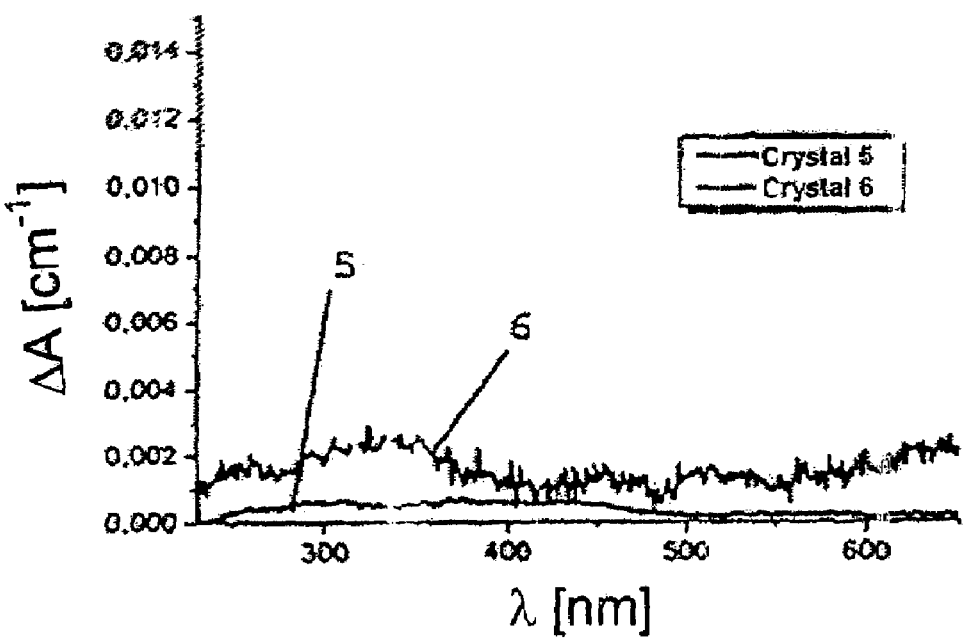
FIG. 3A is a graphical illustration showing two difference spectra for crystals 5 and 6 measured in the second HE testing step of the method according to the present invention.
Figure 3B:
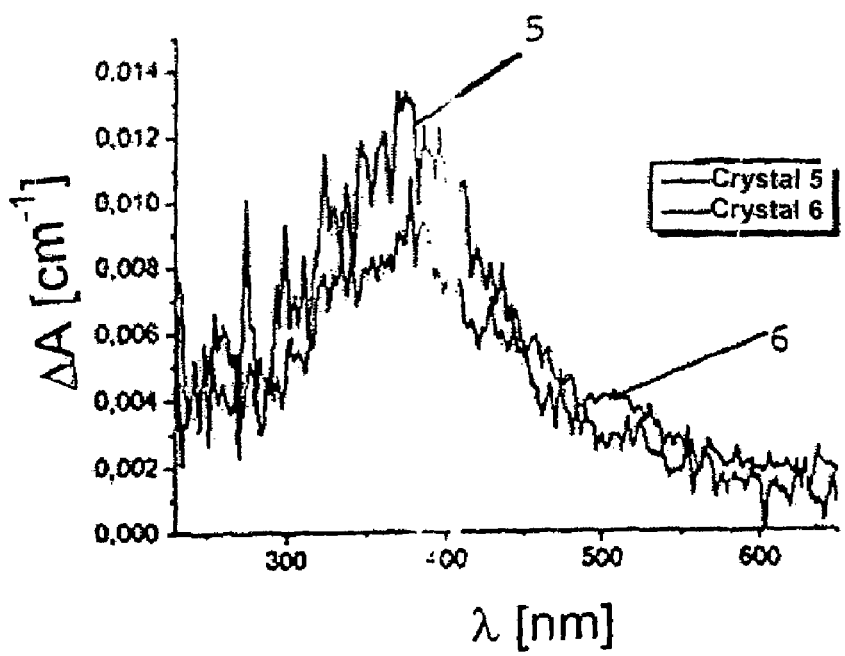
FIG. 3B is a graphical illustration showing two difference spectra for crystals 5 and 6 measured in the third X-ray irradiation testing step of the method according to the present invention.

| | $k_0$, ABSORPTION AT 0 ENERGY DENSITY &$\Delta k_0$ DUE TO IRRADIATION | |
|---|---|---|
| | Prior to Irradiation $k_0$ [$10^{-4}$ cm$^{-1}$] | Change due to Irradiation $\Delta k_0$ [$10^{-4}$ cm$^{-1}$] |
| Crystal 4 | 1.4 | 4 |
| Crystal 3 | 1.1 | 10 | b) It has been shown that the determination of the XRD value according to test 3 alone is not sufficient for determination of the long-term laser stability. For this purpose the HE test 2 (FIG. 3A) and the X-Ray Irradiation Test (Test 3) (FIG. 3B) were performed on the crystals 5 and 6. Crystal 6 had poorer properties as shown by the HE test 2, although crystal 6 did have only slightly poorer properties in the XRD test 3. The formation of the difference spectra for these crystals is shown in Table 3.

TABLE III

| | $k_0$, ABSORPTION AT 0 ENERGY DENSITY &$\Delta k_0$ DUE TO IRRADIATION | |
|---|---|---|
| | Prior to Irradiation $k_0$ [$10^{-4}$ cm$^{-1}$] | Change due to Irradiation $\Delta k_0$ [$10^{-4}$ cm$^{-1}$] |
| Crystal 6 | 4.5 | 4.5 |
| Crystal 5 | 0.8 | 2.4 |

The table shows that the crystal 6 has a clearly stronger absorption change during long-term irradiation than the crystal 5.

This proves that other radiation-induced damage of the optical material can be detected by means of the method according to the invention than with current prior art methods and indeed that long-term radiation-induced damage that occurs over a much longer usage period of for example ten years and after many hundreds of million laser shots can be detected by the method of the invention. The procedure according to the invention may be performed with all three tests over a time interval of less than a day.

While the invention has been illustrated and described as embodied in a method for determination of irreversible radiation damage of optical materials, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of determining an extent of irreversible radiation damage of an optical material, said method comprising the steps of:
    a) irradiating an optical material to be tested with ultraviolet radiation at a wavelength below 250 nm and determining non-intrinsic fluorescence intensity at a wavelength of 740 nm;
    b) irradiating the optical material to be tested with laser light and measuring a change in respective absorptions at a wavelength of 385 nm before and after irradiation; and
    c) irradiating the optical material to be tested with an energetic radiation source until saturation is achieved and measuring a difference of respective surface integrals of corresponding absorption spectra in ultraviolet spectral and/or visible spectral regions before and after irradiation with said energetic radiation source;
    wherein said energetic radiation source is an X-ray source or a radioactive source.

2. The method as defined in claim 1, wherein said wavelength of said ultraviolet radiation below 250 nm is 193 nm.

3. The method as defined in claim 1, wherein said determining said non-intrinsic fluorescence intensity is performed within a predetermined time interval after an end of the irradiating at said wavelength below 250 nm and said predetermined time interval corresponds to 80% of a decay time of said fluorescence intensity.

4. The method as defined in claim 1, further comprising determining intrinsic fluorescence intensity at 285 nm as well as determining said non-intrinsic fluorescence intensity at 740 nm, and then determining a ratio of the non-intrinsic fluorescence intensity to the intrinsic fluorescence intensity, said ratio providing a measure of optical quality of the optical material.

5. The method as defined in claim 1, wherein said laser light has a high energy density of from 25 to 150 mJ/cm$^2$ and during the irradiating with said laser light the optical material is irradiated with from 3 to 20×10$^4$ laser pulses of said laser light.

6. The method as defined in claim 5, wherein said laser light has a wavelength of 193 nm and is produced by an ArF laser.

7. The method as defined in claim 1, wherein said difference of said respective surface integrals of said corresponding absorption spectra is determined between respective wavelength limits of 240 nm and 300 nm.

8. The method as defined in claim 1, wherein a change in respective absorption at 265 nm before and after irradiation is measured when the optical material is irradiated with said energetic radiation source until said saturation is achieved.

9. The method as defined in claim 1, further comprising pre-irradiating the optical material prior to performing said steps with at least 3000 laser pulses so that an absorption state of the optical material associated with rapid reversible radiation damage is saturated.

10. The method as defined in claim 1, wherein the optical material is an alkali halide crystal, an alkaline earth halide crystal, or a mixed crystal.

11. A method of determining an extent of permanent radiation damage of an optical material, said method comprising the steps of:
    a) irradiating an optical material to be tested with ultraviolet radiation at an excitation wavelength below 250 nm, determining intrinsic fluorescence intensity at 285 nm and non-intrinsic fluorescence intensity at a wavelength of 740 nm, and subsequently determining a ratio of the non-intrinsic fluorescence intensity to the intrinsic fluorescence intensity;
    b) if said ratio determined in step a) is below a predetermined limiting value, then irradiating the optical material to be tested with laser light and measuring a change in respective absorptions at a wavelength of 385 nm before and after irradiation;
    c) if said ratio determined in step a) is below said predetermined limiting value, then irradiating the optical material with an energetic radiation source until saturation is achieved and measuring a difference of respective surface integrals of corresponding absorption spectra in ultraviolet spectral and/or visible spectral regions before and after irradiation with said energetic radiation source; and
    d) establishing that the permanent radiation damage of the optical material is sufficiently small for making optical components for lithographic applications from the optical material when said change in step b) and said difference in step c) are below respective limiting values.

12. The method as defined in claim 11, wherein said excitation wavelength of said ultraviolet radiation below 250 nm is 193 nm, said determining of said non-intrinsic fluorescence intensity is performed within a predetermined time interval after an end of the irradiating at said excitation wavelength, and said predetermined time interval corresponds to 80% of a decay time of said non-intrinsic fluorescence intensity.

13. The method as defined in claim 11, wherein said difference of said respective surface integrals of said corresponding absorption spectra is determined between respective wavelength limits of 240 nm and 300 nm.

14. The method as defined in claim 11, wherein said laser light is generated by an ArF laser and has a wavelength of 193 nm, said laser light has a high energy density of from 25 to 150 mJ/cm$^2$, and during the irradiating with said laser light the optical material is irradiated with from 3 to 20×10$^4$ laser pulses of said laser light.

15. The method as defined in claim 11, wherein the optical material is an alkali halide crystal, an alkaline earth halide crystal, or a mixed crystal.

* * * * *